United States Patent [19]
Buckner et al.

[11] Patent Number: 5,359,945
[45] Date of Patent: Nov. 1, 1994

[54] BALANCED PRESSURE SOLID FUEL HEATING UNIT

[75] Inventors: Carrol E. Buckner, Fletcher; Carrol D. Buckner, Hendersonville, both of N.C.

[73] Assignee: Dovetech, Inc., Fletcher, N.C.

[21] Appl. No.: 218,033

[22] Filed: Mar. 25, 1994

Related U.S. Application Data

[63] Continuation of Ser. No. 15,029, Feb. 8, 1993, abandoned, which is a continuation of Ser. No. 628,158, Dec. 17, 1990, abandoned.

[51] Int. Cl.[5] ............................................. F23B 7/00
[52] U.S. Cl. ................................. 110/233; 110/102; 110/110; 110/160; 110/297; 110/314; 110/320; 110/341; 126/58; 126/146
[58] Field of Search ............... 110/396, 102, 233, 108, 110/110, 194, 317, 320, 160, 300, 314, 297, 341; 126/58, 146

[56] References Cited

U.S. PATENT DOCUMENTS

| | | | |
|---|---|---|---|
| 1,604,271 | 10/1926 | Friedman | 110/160 |
| 1,952,023 | 3/1934 | Reeves | 126/146 |
| 2,393,855 | 1/1946 | Cheasley | 126/146 |
| 4,285,325 | 8/1981 | Bellaff | 110/160 X |
| 4,312,278 | 1/1982 | Smith et al. | 110/102 X |
| 4,454,827 | 6/1984 | Smith et al. | 110/102 X |
| 4,545,309 | 10/1985 | Comtois | 110/102 X |
| 4,565,184 | 1/1986 | Collins et al. | 110/110 X |
| 4,782,765 | 11/1988 | Miller et al. | 110/110 X |
| 4,941,414 | 7/1990 | Carlson | 110/108 |
| 5,001,993 | 3/1991 | Gramlow | 110/233 |

*Primary Examiner*—Edward G. Favors
*Attorney, Agent, or Firm*—Wigman, Cohen, Leitner & Myers

[57] ABSTRACT

A method and apparatus for a pellet fuel burning heating unit for burning corn or wood pellets having a balanced pressure system having a four-way split combustion intake airstream. The invention includes a combustion air blower system for providing combustion air into a firebox containing a burner under positive pressure and at the same time providing a negative pressure to remove the combustion gases from the firebox. A pressure regulator and air splitter maintains a balance between the positive and negative pressure and adjusts the air flow into the firebox and out the exhaust. The exhaust is provided through a bank of exhaust tubes running from the top of the firebox to an exhaust manifold. The blower air moves into the pressure regulator and air splitter dividing the air flow such that a portion enters the heating unit exhaust manifold to produce a negative pressure and the remaining portion enters the heating unit burner under positive pressure. Such remaining positive pressure portion is split three ways, with a flow stream directed at the fuel bed in the burner, a flow stream directed concentrically with a fuel pellet feed toward the region directly above the burner and a flow stream directed along the firebox door window, resulting in turbulence and improved combustion efficiency and self-regulation as between the relative amounts of air between the burner fuel bed and the region above the burner.

45 Claims, 9 Drawing Sheets

BALANCED PRESSURE SOLID FUEL HEATING UNIT

This is a continuation of co-pending application Ser. No. 08/015,029 filed on Feb. 8, 1993, abandoned which is a continuation of Ser. No. 07/628,158 filed Dec. 17, 1990, abandoned.

FIELD OF THE INVENTION

The present invention relates to solid fuel heating units and more particularly, to heating units that utilize pellet type fuel.

BACKGROUND OF THE INVENTION

The use of wood burning stoves is very common particularly in those areas where wood logs can be secured fairly inexpensively. In urban areas, the use of wood as an energy source is not as popular because the cost of wood is high and also because the use of wood logs is considered by many to be an annoyance requiring constant cleaning of the area around the heating unit and the need to constantly bring the wood logs to the unit. Also, the problems involving creosote build-up and the release of hydrocarbon pollutants into the atmosphere have dissuaded many people away from the use of wood or coal as an energy source.

To overcome the aforementioned problems, attempts have been made to develop heating units that would burn a cleaner, easier to handle fuel such as wood pellets. The concept was that the pellets could be packaged in a bag and readily purchased at a neighborhood store. The heating units had a hopper that would hold a large supply of the pellets and the pellets would be automatically fed into the burner thereby relieving the user of the need to constantly move logs into the heating unit. U.S. Pat. Nos. 4,513,671 and 4,517,903 show pelletized wood furnaces.

The wood pellet heating unit has not met with a great deal of success for several reasons. The supply of the fuel source is dependent upon a limited number of producers and many potential users may have concerns of having a readily available supply. Also, the heating units have not been as efficient with respect to the fuel burning and the heat output as the more typical wood log heating units. One technical problem is with the methods of providing air for the fuel. Most pellet heating units use a blower to move outside air, either from the area surrounding the unit or from the outside of the building, into the burner portion of the heating unit. If the blower is located upstream of the burner, the unit is said to be positive pressure since the firebox will have a pressure greater than atmospheric. U.S. Pat. No. 4,517,903 is a positive pressure system since the blower is located in the fuel burner and the combustion air is pushed into the burner area. U.S. Pat. No. 4,513,671 is a negative pressure system since the blower is located beyond the fuel burner and the combustion air is essentially sucked into the burner with the firebox having a pressure slightly less than atmospheric.

The use of either positive or negative pressure presents several problems that may contribute to lack of acceptance of the pellet heating units. With the positive pressure unit, the firebox is under pressure so that when the door or other access to the firebox is opened, smoke and other matter will be pushed into the room. In the negative pressure unit, there is a tendency for the blower to clog from the particulate material in the exhaust gases and also a considerable amount of heat is sucked out of the heating unit into the exhaust pipe tending to generate a fairly high temperature at the exhaust pipe.

Attempts have been made to provide both a positive and negative pressure distribution in a firebox. For example, U.S. Pat. No. 1,604,271 to Friedman provides this in a furnace by splitting intake air into two streams, one directed through the grate of the firebox, and the other to the combustion exhaust stream to create a draft in the exhaust.

Thus there exists a need for a pellet fuel heating unit that can overcome all of the aforementioned problems. An object of this invention is to provide a heating unit having a balanced pressure system that will not only burn wood pellets but will burn a pellet-like fuel that is readily available, will burn cleaner than wood pellets, and is inexpensive, namely, shelled corn or corn kernels. The use of corn kernels, primarily U.S. Department of Agriculture grades 1 through 3 feed corn, provides the user with an inexpensive, clean and readily available fuel. It is estimated that there are over 4 billion bushels of suitable feed corn in storage facilities throughout the country and the supply is growing daily.

As shelled corn or corn kernels require a high temperature in order to burn properly without, in essence, self-extinguishing, a highly turbulent combustion air flow to the fuel is required which encompasses each kernel. Thus, a further object of the invention is to provide a heating unit having a turbulent combustion air flow to the area in which the fuel is burned.

It is yet another object of this invention to provide a pellet fuel heating unit that uses both a negative and positive pressure system and avoids the problems associated with either type of system.

Another object of this invention is to provide a heating unit which reduces the fouling and discoloration of the heating unit firebox window.

Still another object of this invention is to provide a heating unit having a high heating efficiency and highly efficient combustion of the fuel.

SUMMARY OF THE INVENTION

The above outlined objectives as well as other objectives and features of the present invention are accomplished by a method and apparatus for a pellet fuel burning heating unit having a balanced pressure system having a four-way split combustion intake airstream.

The method of the present invention includes the steps of containing a combustion zone; providing fuel pellets to be burned in the combustion zone; holding the fuel to be burned in the combustion zone; providing air to the combustion zone in at least two air flow streams, with a first air flow stream directed at the bottom of means provided for holding fuel and a second air flow stream directed at a region above the means provided for holding fuel; removing combustion gases from the combustion zone; and directing air past means provided for removing the combustion gases and into a space to be heated. The method further comprises the steps of providing a suction air exhaust flow from the combustion zone; providing fuel pellets concentric with the second air flow stream, thus preventing smoke and flame from entering means for providing the fuel pellets; providing a third air flow stream directed along a combustion zone door having a window with the air flow stream directed essentially along the window such that soot and combustion product buildup is reduced.

The method of burning fuel pellets includes the steps of providing an air flow stream directed from beneath a firebed, providing an air flow stream directed around the firebed into a region directly above the firebed and providing an air flow stream directed from above into a region directly above the firebed.

The apparatus includes a combustion air blower system for providing combustion air into a firebox containing a burner under positive pressure and at the same time providing a negative pressure to remove the combustion gases from the firebox. A pressure regulator and air splitter maintains a balance between the positive and negative pressure and adjusts the air flow into the firebox and out the exhaust. The exhaust is provided through a bank of exhaust tubes running from the top of the firebox to an exhaust manifold. The exhaust tubes are preferably arranged in a staggered array, resulting in a triangular tube array. The blower air moves into the pressure regulator and air splitter dividing the air flow such that a portion enters the heating unit exhaust manifold to produce a negative pressure and the remaining portion enters the firebox under positive pressure. Such positive pressure portion is split three ways in the pressure regulator and air splitter prior to entry into the firebox. A first flow stream is directed to a plenum formed below the fuel bed in the burner, a second flow stream is directed concentrically with a fuel pellet feed toward the region directly above the burner and a third flow stream is directed along the firebox door window. This flow split results in improved combustion efficiency of the fuel pellets and is self-regulating as between the relative amounts of air between the burner fuel bed and the region above the burner. The burner configuration permits air flow up through the firebed and around the sides of the firebed, such that as clinker buildup occurs, air flow reduction from below is compensated by additional air flow around the sides. The flow directed above the burner is concentric with the fuel feed line and hence reduces the likelihood of flame or smoke entering the fuel feed lines. The combination of air flow through the burner and directly above the burner results in a turbulence which ensures each corn kernel or pellet of fuel is sufficiently surrounded by combustion air to efficiently burn each kernel or pellet. The flow along the firebox door window prevents buildup of soot or discoloration of the glass in the door. A second, room air blower system is provided which directs ambient air around the exhaust tube bank and through vents in the heating unit housing into the room or space to be heated. The exhaust manifold and tube bank arrangement provides improved heating efficiency. The exhaust tube flow is subject to a volume reduction in the exhaust manifold. This results in increased tube heatup and hence higher heat transfer from the heating unit to the room or space to be heated. In addition, as a result of the staggered tube bank array, the air flow inside the housing is turbulent as it contacts the firebox and tube bank before passing through the vents, thereby increasing heat transfer and heating efficiency.

BRIEF DESCRIPTION OF THE DRAWINGS

For a full understanding of the nature and objectives of the invention, reference should be made to the following detailed description taken in conjunction with the accompanying drawings in which.

DETAILED DESCRIPTION OF THE INVENTION

Figure 1:
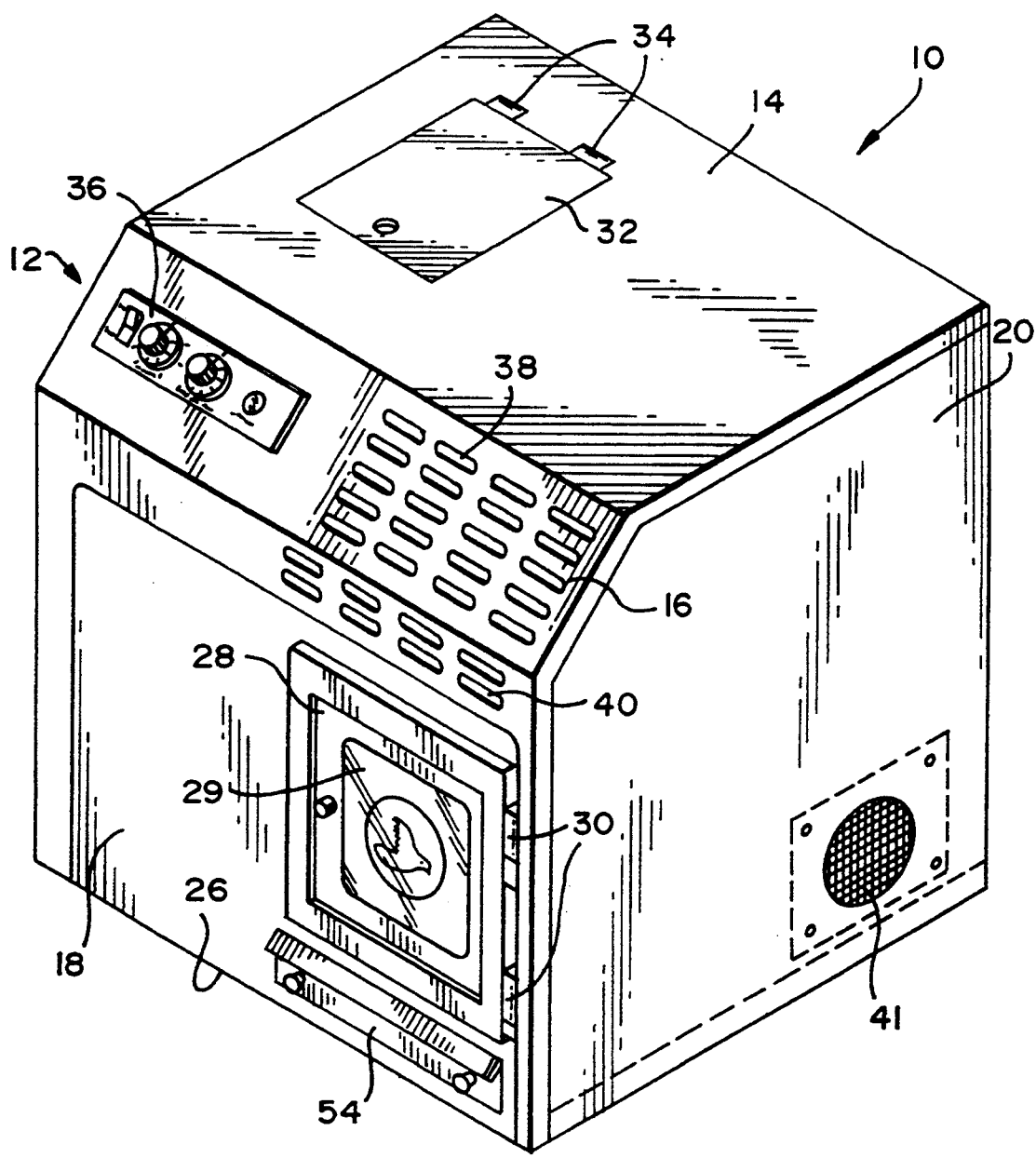
FIG. 1 is a perspective view of the front and side of a heating unit of a preferred embodiment of the present invention.

Referring now to the drawings in detail, wherein like reference numerals indicate like parts throughout the several figures, a preferred embodiment of a pellet fuel burning heating unit of the method and apparatus of the present invention is designated generally by the reference numeral 10.

Figure 2:
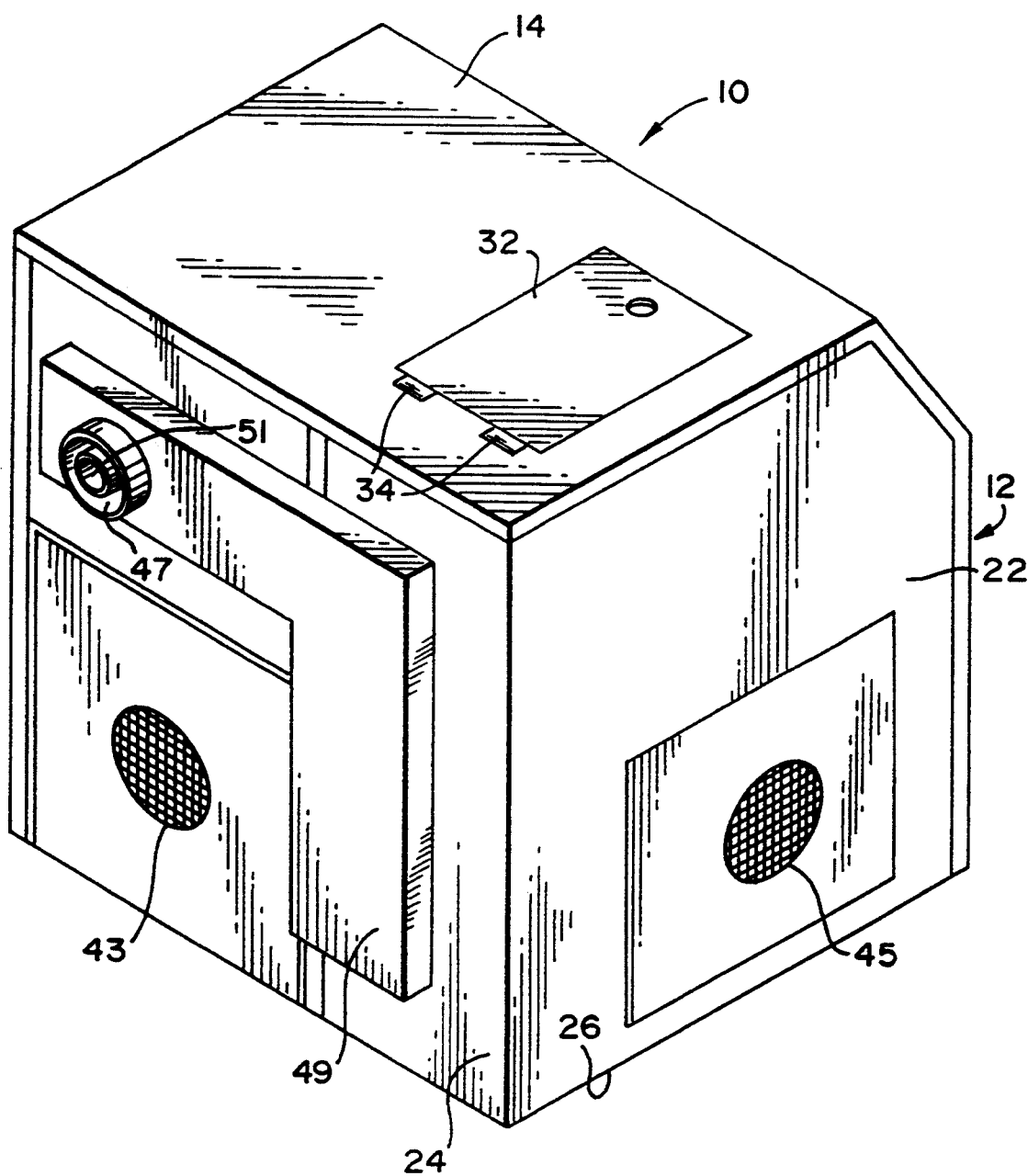
FIG. 2 is a perspective view of the rear and side of a heating unit of a preferred embodiment of the present invention.

FIGS. 1 and 2 show perspective views of the heating unit 10 of the present invention. FIG. 1 shows the front, top and right side of the heating unit 10. FIG. 2 shows the rear, top and left side of the heating unit 10.

As shown in FIGS. 1 and 2, the heating unit 10 includes a housing 12 comprising top wall 14, sloping vent wall 16, front wall 18, side walls 20, 22, rear wall 24 and bottom wall 26. A door 28 having a window 29 is mounted by hinges 30 to front wall 18. A hopper door 32 is mounted by hinges 34 to top wall 14. Control panel 36 is disposed in sloping vent wall 16. Room air vents 38 are disposed within vent wall 16 and room air vents 40 are disposed within front wall 18. Room air intake vent 41 is disposed in housing wall 20; vent 43 is disposed in rear wall 24, and vent 45 is disposed in side wall 22. Combustion air intake 47 is formed in combustion air intake duct 49, mounted on rear wall 24. Exhaust duct 51 is mounted to pass concentrically through combustion air intake 47. Thus, there is countercurrent flow of exhaust gases and combustion air over a short distance. The duct 49 is mounted on the back of the heating unit. The combined duct 49 mounting and countercurrent flow results in a degree of preheating of the combustion air. Ash bin 54 is disposed beneath door 28 on front wall 18.

Figure 3:
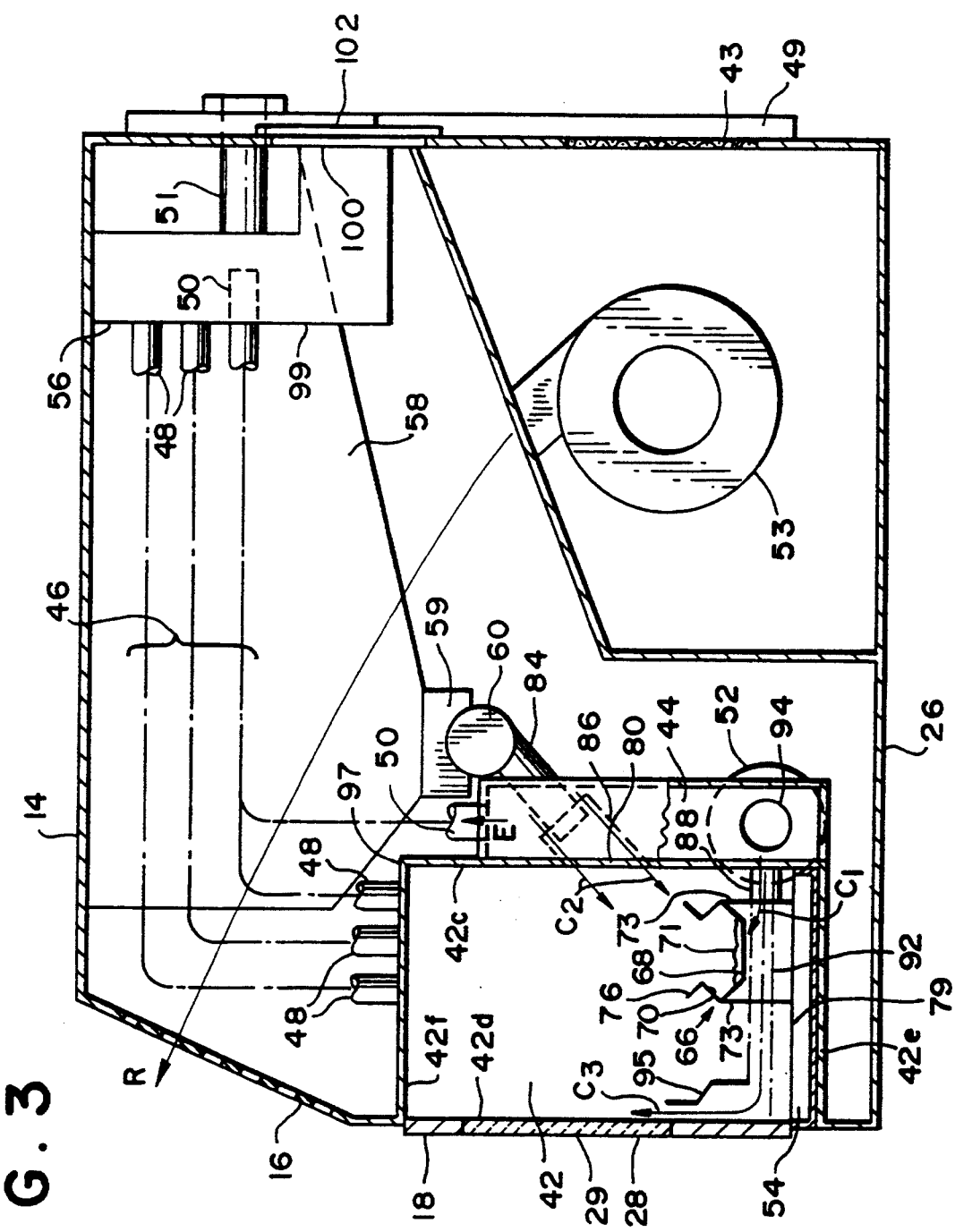
FIG. 3 is a sectional side elevation view of a heating unit through a pressure regulator and firebox of a preferred embodiment of the present invention with the partition between the hopper and combustion areas removed.
Figure 4:
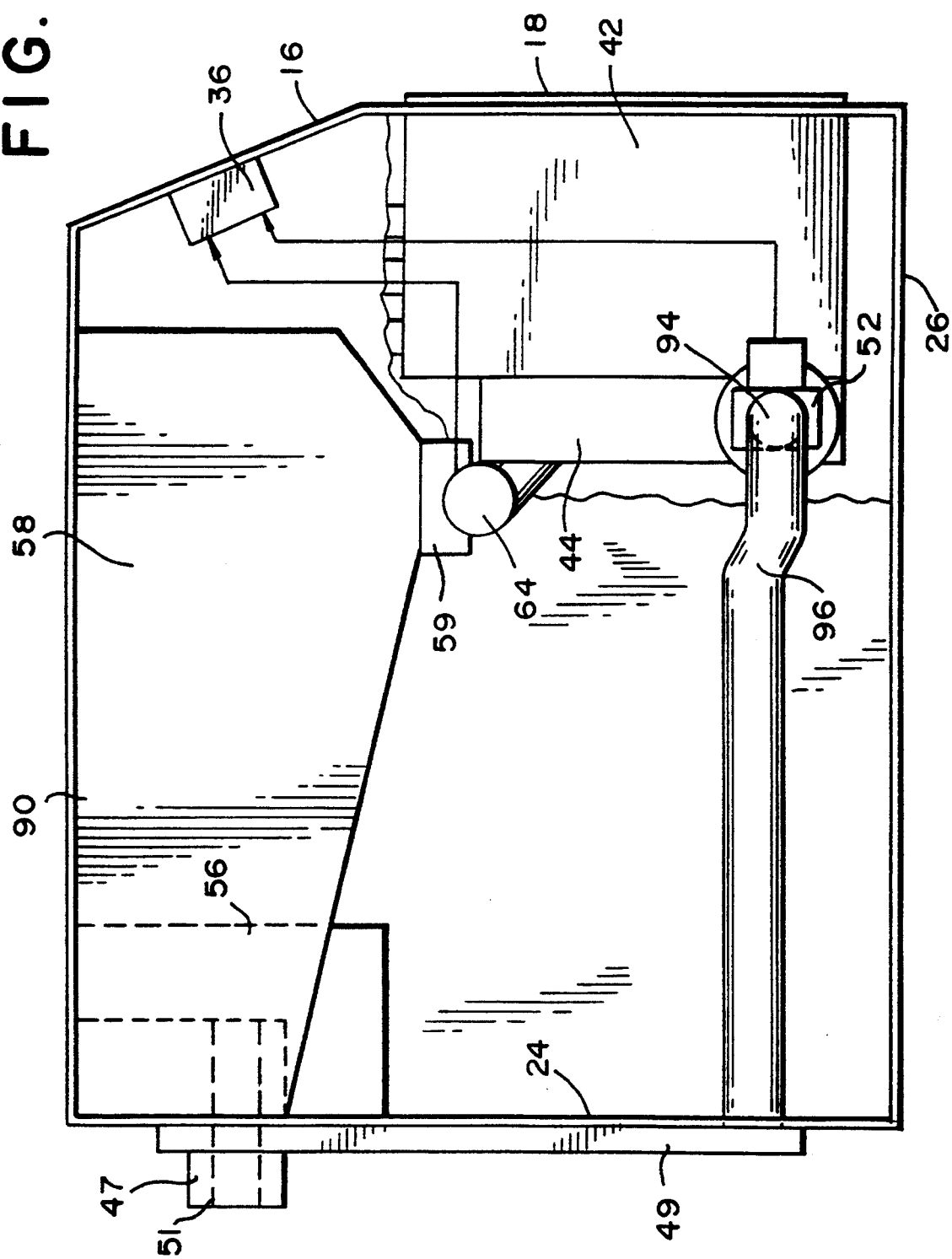
FIG. 4 is a side elevation view of the hopper side of a heating unit, with the housing side wall removed, of a preferred embodiment of the present invention.
Figure 5:
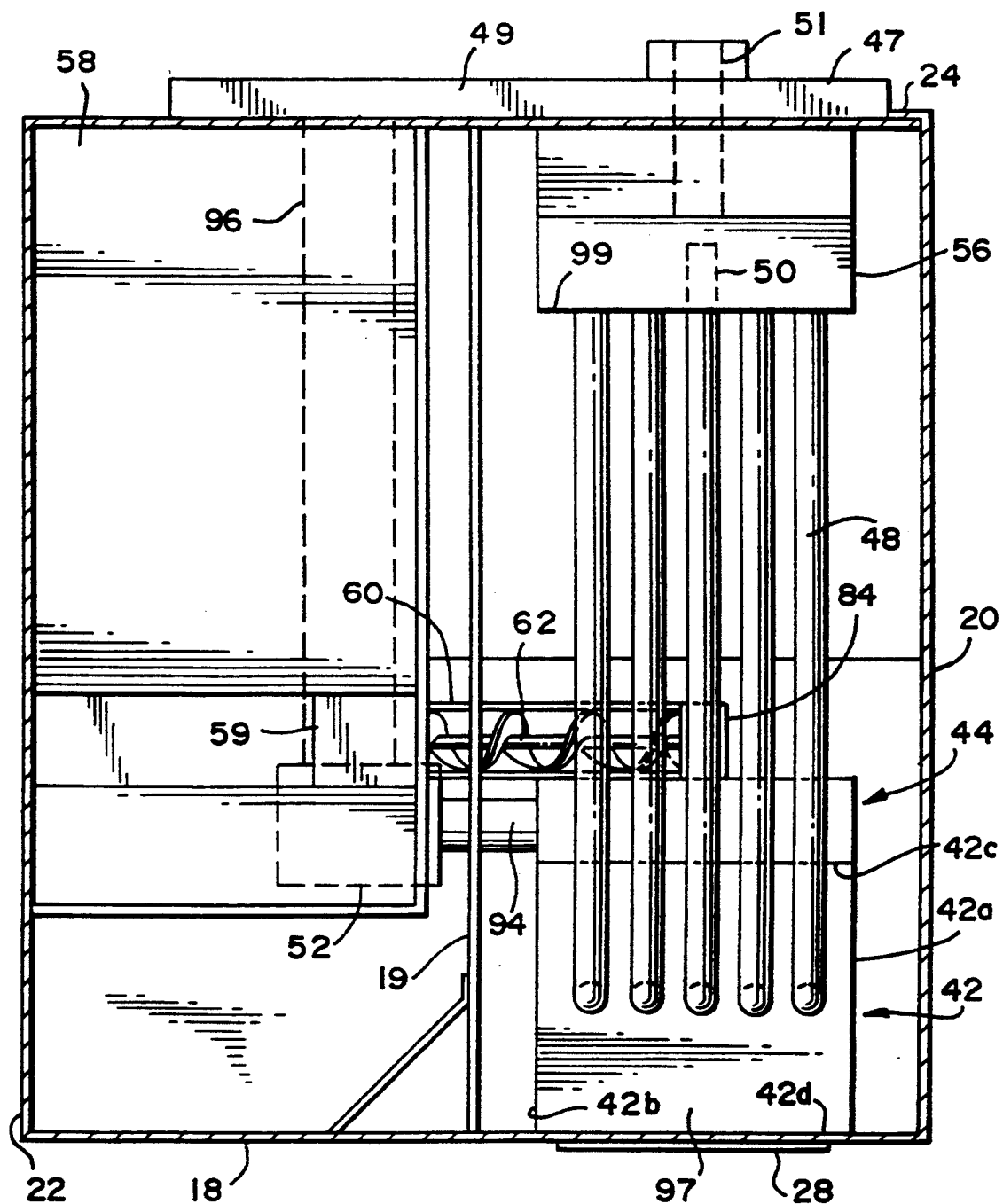
FIG. 5 is a top plan view of a heating unit of a preferred embodiment of the present invention.

As shown in FIGS. 3, 4, and 5, housing 12 encloses a combustion chamber or firebox 42 for containing a combustion zone, an air supply duct or pressure regulator and air splitter 44 ("pressure regulator 44"), a tube bank 46 comprised of a plurality of exhaust tubes 48, a combustion air bypass tube 50, a combustion air blower 52, a room air intake blower 53, and an exhaust manifold 56 connected to the firebox 42 by tube bank 46. Exhaust manifold 56 has cleanout plate 102 disposed at the rear wall thereof. Also enclosed within housing 12 is a hopper 58 which is attached to feed pelletized fuel such as corn kernels or wood pellets to the firebox 42 by a hopper chute assembly 59 to an auger channel 60 which houses a screw auger 62, driven by auger motor 64. Fuel is added to hopper 58 through door 32. A partition 19 separates the hopper 58 area from the pressure regulator 44 and firebox 42 area.

Figure 7:
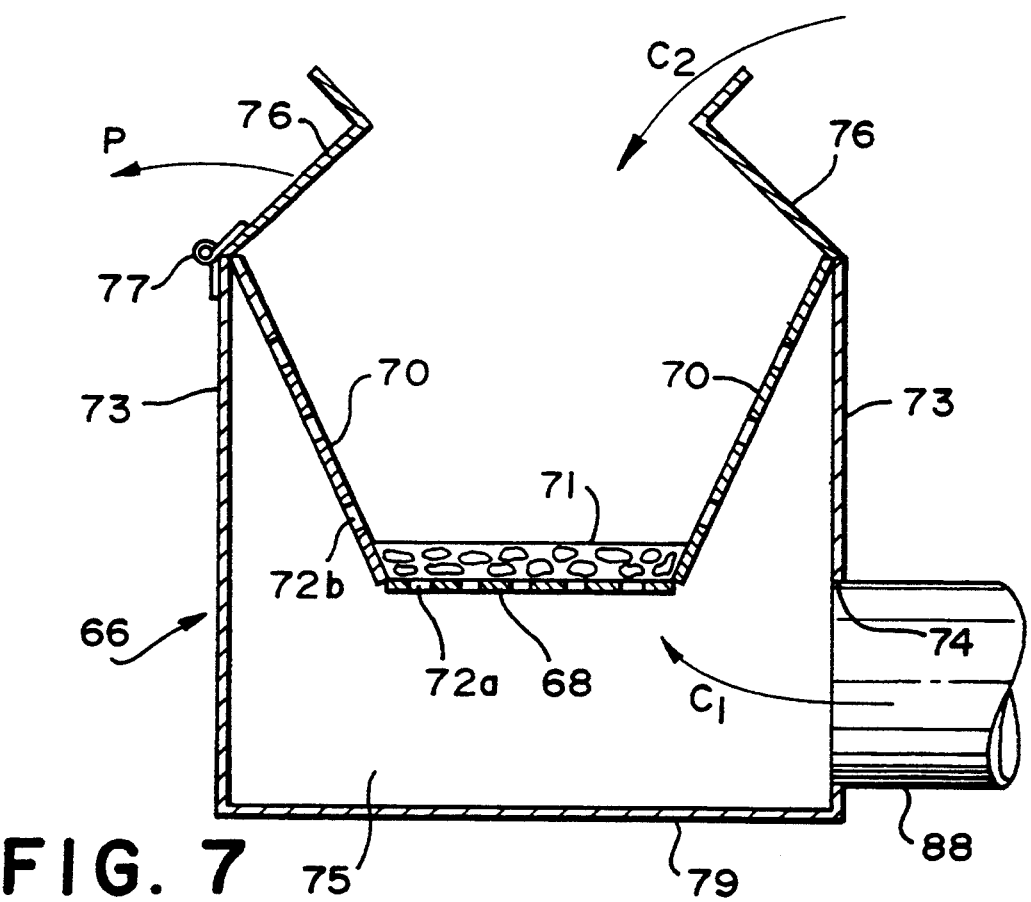
FIG. 7 is a sectional side view of a burner of a heating unit of a preferred embodiment of the present invention.
Figure 8:
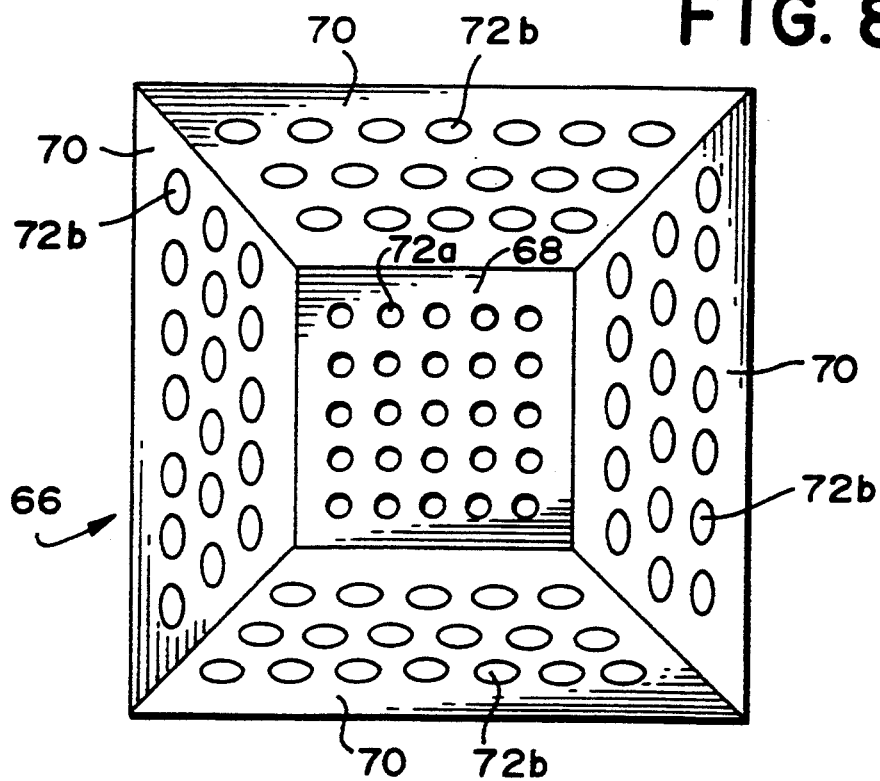
FIG. 8 is a top plan view of a burner of a heating unit of a preferred embodiment of the present invention.

Firebox 42 is formed by side walls 42a, 42b, rear wall 42c, front wall 42d, bottom wall 42e and top wall 42f. Access to firebox 42 is through door 28. Mounted in the firebox 42 is burner 66. As shown in FIGS. 7 and 8, burner 66 is comprised of firebed bottom plate 68, having air holes 72a disposed therein and firebed wall plates 70, having air holes 72b disposed therein. Firebed bottom plate 68 and firebed wall plates 70 define a firebed 71 having an inverted frustopyramidal volume, open at the top to receive fuel. The arrangement of the walls and holes results in air flow up from plenum 75 through firebed 71 and also around firebed 71 and into the region above firebed 71, thereby enhancing turbulence. Thus, as clinker buildup occurs in firebed 71, air flow reduction from below is compensated by additional air flow around the sides of firebed 71. Wall plates 70 are preferably sloped at an angle of approximately 60 degrees from the horizontal. Firebed wall plates 70 are attached to burner side walls 73 to form a support enclosed at the bottom by base plate 79. Disposed within one of burner side walls 73 is air intake opening 74 which feeds the air plenum 75 defined by walls 73 beneath firebed 71. A cowling 76 is pivotally attached to the rim of firebed 71 by hinge 77 to permit access for cleaning the clinker from firebed 71, as shown by arrow P (FIG. 7). Cowling 76 is convergent and divergent in shape and serves to keep air within the region directly above firebed 71 and to enhance turbulence. Ash bin 54 is located beneath burner 66 to collect the combustion ashes falling from the exhaust air leaving the burner 66.

Figure 6:
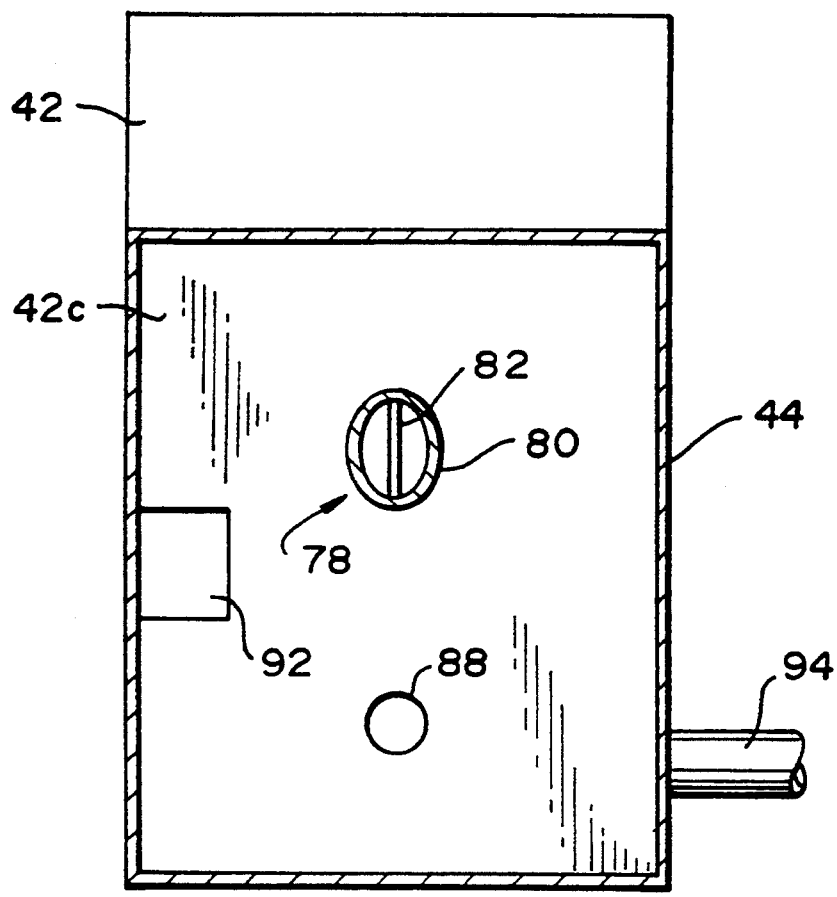
FIG. 6 is a rear view of the front panel of the pressure regulator as it interfaces the firebox of a heating unit of a preferred embodiment of the present invention.
Figure 11:
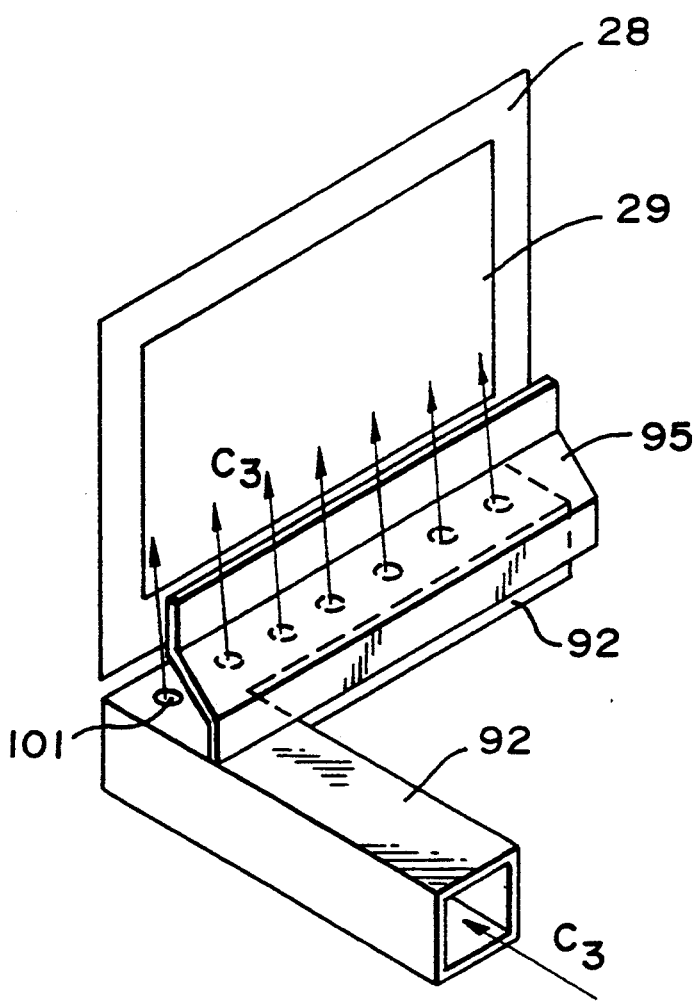
FIG. 11 is a perspective view of an air channel for directing air against a firebox door window.

As shown in FIG. 6, a fuel pellet inlet 78 is located in rear firebox wall 42c above burner 66 and is comprised of an elliptical hole 80 having a vertical fuel pellet distributor bar 82 disposed therein. As shown in FIG. 3, attached to the rear wall 42c of firebox 42 is fuel pellet inlet line is 84 which is concentric with, and passes through, pressure regulator sleeve 86 aligned with hole 80. Combustion air is drawn through the annulus formed between the inlet line 84 and pressure regulator sleeve 86. This reduces the likelihood that smoke or flame will enter the fuel inlet line 84. Combustion inlet duct 88 runs from pressure regulator 44 to burner air plenum 75. Burner 66 is removably mounted above firebox bottom wall 42e such that ash bin 54 is disposed beneath burner 66. As shown in FIG. 3, air channel 92 is disposed along the side and above the base of firebox 42. Air channel 92 is connected to and extends from pressure regulator 44 and has angled plate 95 which deflects air against window 29. As shown in FIG. 11, air channel 92 is essentially rectangular in cross-section, having inside dimensions of approximately 1.75 inch by 0.75 inch, and is L-shaped, having a length of approximately 8.25 inches extending from rear firebox wall 42c to front firebox wall 42d and a length of approximately 11.50 inches extending along wall 42d. There are preferably 21 holes 101 of 0.187 inch inside diameter which allow air to pass between angled plate 95 and window 29.

The transition from a broader to narrower channel results in an increase in air velocity directed along window 29. The angle plate 95, having an edge essentially parallel to window 29, directs the air flow $C_3$ in an essentially fan shape along the window 29.

Hopper 58 is comprised of walls 90 forming a generally downwardly sloping holder for pelletized fuel such as wood pellets or corn. Mounted below hopper 58 is auger channel 60 having a screw auger 62 disposed therein and driven by motor 64. A hopper chute assembly 59 connects hopper 58 to auger channel 60. Auger channel 60 is preferably a generally tubular element having a generally cylindrical arcuate section removed therefrom to accommodate hopper chute assembly 59 and an essentially circular hole provided therein to attach to fuel inlet line 84. The fuel pellets are gravity fed to the auger 62, which in turn meters the pellets to the burner 66.

Figure 10:
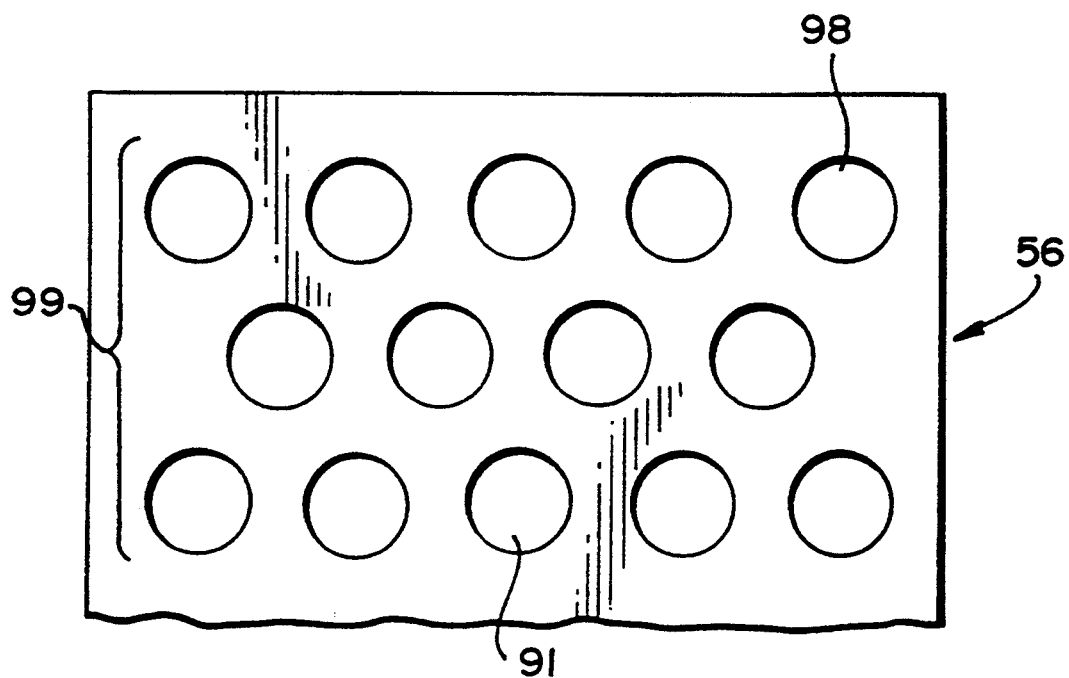
FIG. 10 is a side elevation view of an exhaust manifold tubesheet for exhaust tubes of a heating unit of a preferred embodiment of the present invention.
Figure 9:
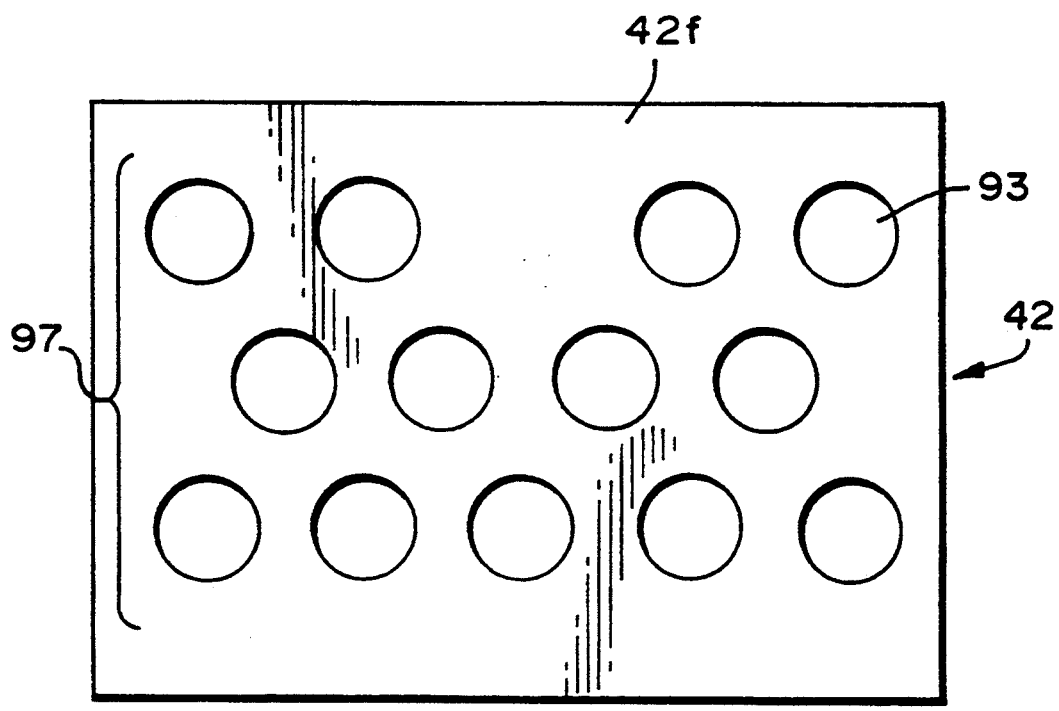
FIG. 9 is a top plan view of a firebox tubesheet for exhaust tubes of a heating unit of a preferred embodiment of the present invention.

As shown in FIGS. 9 and 10, exhaust tubes 48 are connected to firebox 42 through corresponding holes 93 in firebox top wall 42f, which forms a tubesheet 97 for the exhaust tubes 48. Tube bank 46 is comprised of three rows of tubes arranged in a staggered array, as demonstrated in the tubesheet 99 of exhaust manifold 56, having holes 98 therein. The first row has five tubes, the second row has four tubes and the third row has four tubes. The third row also has a bypass tube hole 91 for the bypass air tube 50, which runs from the top of pressure regulator 44 to exhaust manifold 56. Exhaust manifold 56 is adapted to be connected to exhaust duct 51 which is concentric with and extends beyond combustion air intake 47, for venting combustion gases outside of the structure in which the apparatus is used. To vent outside the structure, a conventional double wall pipe (not shown) is connected to exhaust duct 51.

Combustion air blower 52 is a shaded pole blower of squirrel case construction, such as a model 4C440, manufactured by Dayton Electric Manufacturing Co., Chicago, Ill. Ambient air is drawn through air inlet line 96 attached between the inlet nozzle of blower 52 and combustion air intake duct 49 (FIG. 2). Vent 45 in wall 22 (FIG. 2) is used to vent the space enclosing hopper 58 and blower 52. Room air intake blower 53 is also a shaded pole blower, of squirrel cage construction, such as model 4C448A, also manufactured by Dayton Electric Manufacturing Co. Ambient air is drawn through room air intake vent 41 disposed in housing side wall 20, into the inlet nozzle of blower 53. Additional air is provided through inlet vent 43.

The operating range for air delivery for blower 52 is approximately 60 cubic feet per minute (cfm) at k free air static pressure (SP), 57 cfm at 0.1 inch SP, 54 cfm at 0.2 inch SP, 49 cfm at 0.3 inch SP, 39 cfm at 0.4 inch SP, and 23 cfm at 0.5 inch SP. The operating range for blower 53 is approximately 465 cfm for free air, 428 cfm at 0.1 inch SP, 396 cfm at 0.2 inch SP, 352 cfm at 0.3 inch SP, 305 cfm at 0.4 inch SP, and 227 cfm at 0.5 inch SP.

Pressure regulator 44 is essentially rectangular parallelopiped in shape having the approximate dimensions of 3 inches in depth, 12 inches in width and 11.6 inches in height and is preferably made of an appropriate heat resistant material such as 12 gage cold quenched heat resistant steel. Firebox 42 is also essentially rectangular parallelopiped in shape and has the approximate dimensions of 8 inches in depth, 12 inches in width and 16.5 inches in height and is preferably made of 12 gage cold quenched heat resistant steel. Exhaust manifold 56 is L-shaped in vertical cross section, having a height of approximately 13 inches, a width of approximately 18 inches, a depth at the top of approximately 3 inches and a depth at the bottom of approximately 6 inches and is equipped with an access opening 100 at the back bottom for cleaning. Exhaust manifold 56 is preferably made of 12 gage cold quenched heat resistant steel.

Burner holes 72a are approximately 0.156 inch in diameter and burner holes 72b are approximately 0.203 inch in diameter. Fuel pellet inlet line 84 is essentially cylindrical and has an inside diameter of approximately 1.375 inches and an outside diameter of approximately 1.50 inches and is oriented at an angle as it passes through pressure regulator 44 such that it has a long length dimension of approximately 5.63 inches and a short length dimension of 4.12 inches. Fuel pellet inlet line 84 is preferably made of 14 gage cold quenched heat resistant steel. Pressure regulator sleeve 86 is essentially cylindrical and has an inside diameter of approximately 1.625 inches and an outside diameter of approximately 1.90 inches. Sleeve 86 is also oriented at an angle such that it has a long length dimension of approximately 3.50 inches and a short length dimension of approximately 1.60 inches. Pressure regulator sleeve 86 is preferably made of 0.145 inch steel pipe. Combustion air inlet line 88 and air intake hole 74 each has an inside diameter of approximately 1.00 inch and line 88 is made of cold quenched heat resistant steel. Hole 80 in pressure regulator 44 and firebox wall 42c is elliptical in shape, having a major inside diameter axis of approximately 2.62 inches and a minor inside diameter axis of approximately 2.02 inches. Air inlet line 96 has an inside diameter of approximately 1.850 inches, a length of approximately 2.50 inches, and is made of cold quenched heat resistant steel. Exhaust duct 51 is approximately 5.12 inches long and has an inside diameter of 2.850 inches and is made of suitable steel tubing. Exhaust tubes 48 are each approximately 1.350 inches in inside diameter and are each made of 14 gage 5050 AL steel. The first row has a length of approximately 23.25 inches. The second row has a length of approximately 19.25 inches. The third row has a length of approximately 16.25 inches. Air bypass tube 50 has an inside diameter of approximately 1.350 inches, is approximately 18.75 inches long and is made of 14 gage 5050 AL steel. Air channel 92 and slanted plate 95 are preferably made of 16 gage cold quenched heat resistant steel.

The operation of the heating unit 10 is as follows:

Fuel is loaded into hopper 58 through hopper door 32. As used herein, "fuel" refers to any pelletized fuel such as wood pellets or corn kernels. However, corn kernels are the preferred fuel. Hopper 58 is sized to hold approximately 70 pounds or 1.25 bushels of corn. The fuel is gravity fed through hopper chute assembly 59 and the auger channel 60 via auger 62, driven by auger motor 64. The fuel then falls through fuel pellet inlet line 84 and is distributed as it exits by fuel pellet distributor bar 82. This results in a more even distribution of the fuel pellets in burner 66. The auger 62 speed and hence fuel flow rate is determined by thermo-static controls, as known in the art, and as provided by control panel 36. This results in a fuel consumption rate range of approximately one pound per hour for a low burn rate to eight pounds per hour for a high burn rate. A moderate fuel consumption rate is 5 to 6 pounds per hour. Thus, fuel consumption is typically one bushel per 18 to 30 hours. The typical combustion temperature which must be maintained to burn corn is of the order of 800° F. The combination of air flow streams directed through the firebed bottom plate 68 and sidewalls 70 of burner 66 and to the region directly above burner 66 results in a turbulence which essentially surrounds each fuel kernel with combustion air and assures proper combustion temperatures and desired combustion efficiency. Furthermore, because of the interrelationship between the pressures in the burner plenum 75, the firebox region above burner 66 and the pressure in pressure regulator 44, as clinker buildup occurs, pressure and flow regulation occurs between air flow to plenum 75 and to the region from above burner 66. Suitable combustion temperatures for other fuels are achieved by proper air flow regulation and fuel flow rates, as readily determined by one skilled in the art.

The heating unit 10 is started by placing wood chips or pellets in firebed 71 and igniting the chips or pellets, using campfire type starter pieces, as is known in the art. During startup, combustion air blower 52 is in operation, providing combustion air to firebox 42 and to air bypass tube 50 to provide exhaust suction flow. The pelletized fuel feed is controlled by standard, known thermostatic control means. When the exhaust tube bank 46 temperature reaches a preset value, indicative of adequate combustion temperature in the burner 66, auger 62 is actuated to feed fuel to burner 66. Room air intake blower 53 is also actuated to provide air flow past tube bank 46 through vents 38, 40 and into the room or space to be heated, when such operating conditions are satisfied.

The present invention provides a high combustion efficiency on the order of 98% by a unique air flow path and pressure regulation technique. Ambient air is drawn into housing 12 through intake duct 96 by blower 52 and blown into pressure regulator 44 through air inlet duct 94. Typical air flow rates are on the order of 60 cfm. This air is then directed in several different flow paths to effect fuel combustion. Air is directed into pressure regulator 44 where it is divided into four streams. The first stream $C_1$, is directed through combustion air inlet line 88 to burner air intake hole 74 into plenum 75 and through holes 72a and 72b. The second stream $C_2$ is directed from pressure regulator 44 through pressure regulator sleeve 86 and is directed into the region directly above burner 66. The third air flow stream is directed through air channel 92 through a plurality of holes therein (not shown) to slanted plate 95 which directs air past window 29 in door 28 to effect a "window wash" to minimize discoloration, soot and combustion product buildup on window 29. The air flow streams $C_1$, $C_2$, and $C_3$ ultimately combine in the upper regions of firebox 42 and are removed through the exhaust tubes 48 of tube bank 46.

The fourth air flow stream from pressure regulator 44, designated as air stream E, is directed through a bypass air tube 50, running from the top of pressure regulator 44 to exhaust manifold 56. This airstream E is mixed with the combustion exhaust air from tube bank 46. This creates a suction flow in the exhaust. Such a mixing has several favorable effects. The exhaust air temperature expelled to the outside is reduced and hence is on the order of that for a clothes dryer. In addition, because there is a transition from a higher volume in the exhaust manifold 56 to exhaust duct 51, there will be a pressure increase, resulting in a flow drop, thereby tending to hold the heat in the exhaust tubes 48, thus increasing the heat transfer to the room to be heated. The flows within the firebox tend to be self-regulating, depending on the fuel pellet feed rates. Typically, somewhat less than ¼ of the air in the firebox is directed toward the region above the burner and ⅜ of the air is directed through the base of the burner. The remaining air is directed through window wash air channel 92. The air going through the burner 66 tends to create a turbulence which envelopes each fuel pellet or kernel of corn. The feeding of combustion air concentric with the fuel line prevents flame and smoke from backing up into the fuel feed channel.

For the room heating flow path, designated by arrow R, air is taken through air inlet duct 41 by intake blower 53 and is circulated around firebox 42 and past exhaust tube bank 46 and heated and then out of vents 38, 40 into the room or other space to be heated. The spacing and arrangement of the tubes in tube bank 46 result in turbulence within the housing 12 and improved heat transfer to the air stream 12 from tube bank 46. Typical air flow rates are on the order of 465 cfm.

Certain preferred materials have been described herein. However, other suitable heat resistant materials, as known in the art, are contemplated.

Although a certain presently preferred embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A fuel pellet burning heating unit comprising:
   (a) means for containing a combustion zone;
   (b) means for providing fuel pellets to be burned in said combustion zone;
   (c) means for holding fuel to be burned in said combustion zone;
   (d) means for providing air to said combustion zone simultaneously from below said combustion zone and from above said combustion zone;
   (e) means for removing combustion gases from said combustion zone containing means; and
   (f) blower means for directing air past said combustion gas removing means and into a space to be heated.

2. A fuel pellet burning heating unit as in claim 1, wherein said means for providing air to said combustion zone further comprises means for providing at least two air flow streams, a first said air flow stream directed at the bottom of said fuel holding means and a second said air flow stream directed at a region above said fuel holding means.

3. A fuel pellet burning heating unit as in claim 1 further comprising means for providing a suction air exhaust flow from said combustion zone.

4. A fuel pellet burning heating unit as in claim 1, further comprising an air heating system including air duct means comprising a plurality of exhaust tubes attached at an exhaust entry end to said combustion zone containing means and at an exhaust outlet end to an exhaust manifold.

5. A fuel pellet burning heating unit as in claim 4, wherein said exhaust tubes are arranged in a staggered array.

6. A fuel pellet burning heating unit as in claim 4, wherein said air provided to said combustion zone and said combustion gases are countercurrent in flow direction over a first distance and said combustion zone air passes along a rear surface of said heating unit, thereby preheating said combustion zone air.

7. A fuel pellet burning heating unit as in claim 1, wherein said air provided to said combustion zone and said combustion gases are countercurrent in flow direction over a first distance and said combustion zone air passes along a rear surface of said heating unit, thereby preheating said combustion zone air.

8. A fuel pellet burning heating unit as in claim 1, wherein said means for holding fuel to be burned comprises a fuel pellet burner having:
   (a) a rectangular base plate having edges;
   (b) four side wall plates attached at bottom edges to the edges of said base plate;
   (c) a rectangular firebed bottom plate having a plurality of holes therein; and
   (d) four firebed wall plates, each having a plurality of holes therein, attached at the edges of said firebed bottom plate, said firebed wall plates and said firebed bottom plate defining an inverted essentially frustopyramidal volume open at the top, and said edges of said wall plates at said top of said open volume attached to top edges of said side wall plates, thereby forming a plenum beneath said frustopyramidal volume.

9. A fuel pellet burning heating unit as in claim 1 further comprising a door having a window therein and wherein said air providing means includes means for providing a third air flow stream directed essentially along said window such that soot and combustion product buildup is reduced.

10. A fuel pellet burning heating unit comprising:
    (a) means for containing a combustion zone;
    (b) means for providing fuel pellets to be burned in said combustion zone;
    (c) means for holding fuel to be burned in said combustion zone;
    (d) means for providing air to said combustion zone in at lest two air flow streams, a first said flow stream directed at the bottom of said fuel holding means and a second said flow stream directed from above at the region above said fuel holding means;
    (e) means for removing combustion gases from said combustion zone containing means; and
    (f) blower means for directing air past said combustion gas removing means and into a space to be heated.

11. A fuel pellet burning heating unit as in claim 10, further comprising an air heating system including air duct means comprising a plurality of exhaust tubes attached at an exhaust entry end to said combustion zone containing means and at an exhaust outlet end to an exhaust manifold.

12. A fuel pellet burning heating unit as in claim 10, further comprising means for providing a suction air exhaust flow from said combustion zone.

13. A fuel pellet burning heating unit as in claim 10, further comprising a door having a window therein and wherein said air providing means includes means for providing a third air flow stream directed essentially along said window such that soot and combustion product buildup is reduced.

14. A fuel pellet burning heating unit as in claim 12, wherein said means for holding fuel to be burned comprises a fuel pellet burner having:
(a) a rectangular base plate having edges;
(b) four side wall plates attached at bottom edges to the edges of said base plate;
(c) a rectangular firebed bottom plate having a plurality of holes therein; and
(d) four firebed wall plates, each having a plurality of holes therein, attached at the edges of said firebed bottom plate, said firebed wall plates and said firebed bottom plate defining an inverted essentially frustopyramidal volume open at the top, and said edges of said wall plates at said top of said open volume attached to top edges of said side wall plates, thereby forming a plenum beneath said frustopyramidal volume.

15. A fuel pellet burning heating unit as in claim 10, comprising a combustion air intake duct aligned to pass countercurrent over a first distance with said combustion gas removing means and to pass along a back surface of said heating unit, thereby preheating said combustion air.

16. A fuel pellet burning heating unit comprising:
(a) a firebox;
(b) a burner means within said firebox;
(c) exhaust duct means to remove combustion gases from said firebox;
(d) air duct means to provide combustion air to said burner means, said combustion air divided into a first air flow stream directed through said burner, a second air flow stream directed from above into a region immediately above said burner means, and a third air flow stream into said exhaust duct;
(e) air supply means to deliver air to said air duct means and to said exhaust duct means; and
(f) blower means for directing air past said exhaust duct means and into a space to be heated.

17. A fuel pellet burning heating unit as in claim 16, further comprising a firebox having a door with a window disposed therein and wherein said air duct means divides said combustion air into a further air flow stream directed past said firebox door window.

18. A fuel pellet burner comprising:
(a) means for holding fuel pellets;
(b) means for directing combustion air through said holding means,
(c) means for directing combustion air around said holding mean into a region above said holding means, and
said means for holding fuel pellets and said means for directing combustion air around said holding means defining walls having a convergent-divergent top opening for receiving combustion air directed from above said holding means.

19. A fuel pellet burner as in claim 18, wherein said means for holding fuel pellets is provided with a plurality of holes for air to pass therethrough.

20. A fuel pellet burner as in claim 18, wherein said means for holding fuel pellets and said means for directing combustion air through said holding means comprise a firebed plate having a plurality of holes therein.

21. A fuel pellet burner as in claim 18, wherein said means for directing air around said holding means comprises one or more plates having a plurality of holes therein and wherein further said fuel pellet holding means is attached to said means for directing air around said holding means, thereby comprising a cavity generally open at the top to receive combustion air directed from above said holding means.

22. A fuel pellet burner as in claim 21, wherein said cavity formed by said fuel pellet holding means and said means for directing air around said holding means is generally in the form of an inverted frustopyramid.

23. A fuel pellet burner as in claim 18, wherein said fuel pellet holding means and said means for directing air around said holding means are attached to enclose an air plenum located beneath said holding means.

24. A fuel pellet burner as in claim 18, further comprising means for holding air in a region directly above said fuel pellet holding means.

25. A fuel pellet burner comprising:
(a) a rectangular base plate having edges;
(b) four side wall plates attached to the edges of said base plate;
(c) a rectangular firebed bottom plate having a plurality of holes therein;
(d) four firebed wall plates, each having a plurality of holes therein, attached at the edges of said firebed bottom plate, said firebed wall plates and said firebed bottom plate defining an inverted essentially frustopyramidal volume open at the top, and said edges of said wall plates at said top of said open volume attached to top edges of said side wall plates, thereby forming a plenum beneath said frustopyramidal volume; and
(e) a convergent-divergent cowling attached to top edges of said side wall plates.

26. A fuel pellet burner as in claim 25, further comprising means for providing combustion air to said plenum and means for providing air to a region directly above said frustopyramidal volume.

27. A method of providing heat by burning fuel pellet comprising the steps of:
(a) containing a combustion zone;
(b) providing fuel pellets to be burned in said combustion zone;
(c) holding fuel to be burned in said combustion zone;
(d) providing air to said combustion zone in at least two air flow streams, a first said flow stream directed at the bottom of means provided for holding fuel and a second said air flow stream directed form above toward a region above means for holding fuel;
(e) removing combustion gases from means provided for containing said combustion zone; and
(f) directing air past means provided for removing said combustion gases and into a space to be heated.

28. A method as in claim 27, further comprising the steps of providing an air heating system including:
(a) air duct means comprising a plurality of exhaust tubes attached at an exhaust entry end to said combustion zone containing means and at an exhaust outlet end to an exhaust manifold; and
(b) blower means for directing air past said exhaust tubes and into a space to be heated.

29. A method as in claim 27 further comprising the step of providing a suction air exhaust flow from said combustion zone.

30. A method as in claim 27 further comprising the step of providing in a combustion zone containing means a door having a window therein and wherein said air providing step includes the step of providing a third air flow stream directed essentially along said window such that soot and combustion product buildup is reduced.

31. A method of providing combustion air to a fuel pellet burner having a firebed comprising the steps of providing an air flow stream directed from beneath said firebed, providing an air flow stream directed around said firebed into a region directly above said firebed and providing an air flow stream directed from above into a region directly above said firebed.

32. A fuel pellet burning heating unit comprising:
(a) means for containing a combustion zone;
(b) means for providing fuel pellets to be burned in said combustion zone.
(c) means for holding fuel to be burned in said combustion zone;
(d) means for providing air to said combustion zone;
(e) means for removing combustion gases from said combustion zone containing means;
(f) blower means for directing air past said combustion gas removing means and into a space to be heated, and
(g) an air heating system including air duct means comprising a plurality of exhaust tubes attached at an exhaust entry end to said combustion zone containing means and at an exhaust outlet end to an exhaust manifold, said exhaust manifold comprising an enclosure having an essentially L-shaped vertical cross-section, adapted to receive a plurality of exhaust tubes and at least one tube providing a suction air flow from said combustion zone.

33. A fuel pellet burning heating unit as in claim 32, wherein said exhaust manifold includes a cleanout plate covering an opening disposed near the base of said L-shaped manifold.

34. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone including means for providing at least two air flow streams, a first said air flow stream directed at the bottom of said fuel holding means and a second said air flow stream directed at a region above said fuel holding means.
(e) means for removing combustion gases from said combustion zone containing means; and
(f) blower means for directing air past said combustion gas removing means and into a space to be heated,
wherein said means for providing fuel pellets is arranged essentially concentrically with said second air flow stream providing means, whereby said concentric fuel pellet and second air flow stream prevents smoke and flame from entering said fuel pellet providing means.

35. A fuel pellet burning heating unit as in claim 34, wherein said means for providing fuel pellets comprises an auger disposed within an auger channel, attached at one end to a fuel hopper, and at another end to a fuel pellet inlet line, and said second air flow stream providing means comprises a tube concentric with said fuel pellet inlet line, and whereby said concentric arrangement provides an annular air flow stream from said means for providing air to said combustion zone to said means for containing a combustion zone.

36. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone;
(e) means for removing combustion gases from said combustion zone containing means;
(f) blower means for directing air past said combustion gas removing means and into a space to be heated;
(g) means for providing a suction air exhaust flow from said combustion zone; and
(h) an exhaust manifold having a volume less than the combined volume of said means for removing combustion gases and for said means for providing suction exhaust flow.

37. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone;
(e) means for removing combustion gases from said combustion zone containing means;
(f) blower means for directing air past said combustion gas removing means and into a space to be heated, and
(g) a door having a window therein,
and wherein said air providing means includes means for providing a third air flow stream directed essentially along said window such that soot and combustion product buildup is reduced, said means for providing a third air flow stream comprises an essentially L-shaped duct having essentially rectangular crosssection, a plurality of holes disposed within said duct and located beneath said window and an angled plate for directing air from said holes against such window.

38. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone in at least two air flow streams, a first said flow stream directed at the bottom of said fuel holding means and a second said flow stream directed at the region above said fuel holding means, wherein said means for providing fuel pellets is arranged essentially concentrically with said second air flow stream providing means, whereby said concentric fuel pellet and second air flow stream prevents smoke and flame from entering said fuel pellet providing means.
(e) means for removing combustion gases from said combustion zone containing means; and
(f) blower means for directing air past said combustion gas removing means and into a space to be heated.

39. A fuel pellet burning heating unit comprising:
(a) means for containing a combustion zone;
(b) means for providing fuel pellets to be burned in said combustion zone;

(c) means for holding fuel to be burned in said combustion zone;
(d) means for providing air to said combustion zone in at least two air flow streams, a first said flow stream directed at the bottom of said fuel holding means and a second said flow stream directed at the region above said fuel holding means;
(e) means for removing combustion gases from said combustion zone containing means;
(f) blower means for directing air past said combustion gas removing means and into a space to be heated;
(g) means for providing a suction air exhaust flow from said combustion zone; and
(h) an exhaust manifold having a volume less than the combined volume of said means for removing combustion gases and said means for providing suction exhaust flow.

40. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone in at least two air flow streams, a first said flow stream directed at the bottom of said fuel holding means and a second said flow stream directed at the region above said fuel holding means;
(e) means for removing combustion gases from said combustion zone containing means;
(f) blower means for directing air past said combustion gas removing means and into a space to be heated; and
(g) a door having a window therein and wherein said air providing means includes means for providing a third air flow stream directed essentially along said window such that soot and combustion product buildup is reduced;
wherein said means for providing a third air flow stream comprises an essentially L-shaped duct having an essentially rectangular cross-section, a plurality of holes disposed within said duct and located beneath said window and an angled plate for directing air from said holes against said window.

41. A fuel pellet burner comprising:
(a) means for containing a combustion zone;
(b) means for providing fuel pellets to be burned in said combustion zone, said means for providing fuel pellets comprising an auger disposed within an auger channel attached at one end to a fuel hopper, and at another end to a fuel pellet inlet line;
(c) means for holding fuel to be burned in said combustion zone;
(d) means for providing air to said combustion zone in at least two air flow streams, a first said flow stream directed at the bottom of said fuel holding means and a second said flow stream directed at the region above said fuel holding means, said second air flow stream providing means comprising a tube concentric with said fuel pellet outlet line;
(e) means for removing combustion gases from said combustion zone containing means; and
(f) blower means for directing air past said combustion gas removing means and into a space to be heated,
whereby said concentric arrangement provides an annular air flow stream from said combustion flow means for providing air to said means for containing a combustion zone.

42. A fuel pellet burner comprising:
(a) means for holding fuel pellets;
(b) means for directing combustion air through said holding means,
(c) means for directing combustion air around said holding means into a region above said holding means, said means for holding fuel pellets and said means for directing combustion air around said holding means defining an opening for receiving combustion air directed from above said holding means; and
(d) means for holding air in a region directly above said fuel pellet holding means, said means for holding air comprising a convergent-divergent cowling pivotally attached to said opening.

43. A fuel pellet burning heating unit comprising:
(a) containing a combustion zone;
(b) providing fuel pellets to be burned in said combustion zone;
(c) holding fuel to be burned in said combustion zone;
(d) providing air to said combustion zone in at least two air flow streams, a first said flow stream directed at the bottom of means provided for holding fuel and a second said air flow stream directed at a region above means for holding fuel;
(e) removing combustion gases from means provided for containing said combustion zone;
(f) directing air past means provided for removing said combustion gases and into a space to be heated,
wherein said step for providing fuel pellets is essentially concentric with said second air flow stream providing step, whereby said concentric fuel pellet provision and second air flow stream prevents smoke and flame from entering a means for providing said fuel pellets.

44. A fuel pellet burning heating unit comprising:
(a) means for containing a combustion zone;
(b) means for providing fuel pellets to be burned in said combustion zone;
(c) means for holding fuel to be burned in said combustion zone;
(d) means for providing air to said combustion zone including a pressure regulator providing at least two air flow streams, a first said air flow stream directed at the bottom of said fuel holding means and a second said air flow stream concentric with said fuel pellet providing means and directed at a region above said fuel holding means;
(e) means for removing combustion gases from said combustion zone containing mean; and
(f) blower means for directing air past said combustion gas removing means and into a space to be heated.

45. A fuel pellet burning heating unit as in claim 44, wherein said pressure regulator provides a third air flow stream directed through said combustion gas removing means.

* * * * *